US009873003B2

(12) United States Patent
Tsunoo et al.

(10) Patent No.: US 9,873,003 B2
(45) Date of Patent: Jan. 23, 2018

(54) X-RAY POSITIONING APPARATUS, X-RAY POSITIONING METHOD, AND ATTENTIONAL IMAGE PHOTOGRAPHING METHOD

(75) Inventors: Takanori Tsunoo, Chiyoda-ku (JP); Nobuhiko Ina, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 260 days.

(21) Appl. No.: 14/400,802

(22) PCT Filed: Jul. 13, 2012

(86) PCT No.: PCT/JP2012/067891
§ 371 (c)(1),
(2), (4) Date: Nov. 13, 2014

(87) PCT Pub. No.: WO2014/010073
PCT Pub. Date: Jan. 16, 2014

(65) Prior Publication Data
US 2015/0131780 A1 May 14, 2015

(51) Int. Cl.
*A61N 5/10* (2006.01)
*A61B 6/00* (2006.01)
(Continued)

(52) U.S. Cl.
CPC ............ *A61N 5/107* (2013.01); *A61B 5/0873* (2013.01); *A61B 5/0878* (2013.01);
(Continued)

(58) Field of Classification Search
CPC ................ A61N 5/1048; A61N 5/1049; A61N 2005/105; A61N 2005/1051;
(Continued)

(56) References Cited

U.S. PATENT DOCUMENTS 5,820,553 A * 10/1998 Hughes ............... A61B 6/08
378/65
5,901,199 A * 5/1999 Murphy ............... A61B 6/08
378/65
(Continued)

FOREIGN PATENT DOCUMENTS

JP 2001-161839 A 6/2001
JP 2005-111151 A 4/2005
(Continued)

OTHER PUBLICATIONS

International Search Report (PCT/ISA/210) dated Aug. 21, 2012, by the Japanese Patent Office as the International Searching Authority for International Application No. PCT/JP2012/067891.
(Continued)

*Primary Examiner* — Allen C. Ho
(74) *Attorney, Agent, or Firm* — Buchanan Ingersoll & Rooney PC (57) ABSTRACT

An X-ray positioning apparatus according to the present invention is provided with an X-ray video device that generates second X-ray image data in which a respiratory signal of a patient and first X-ray image data are related to each other, a positioning computer that generates patient platform control data for controlling a patient platform, and a photographing trigger generation apparatus that outputs a photographing trigger signal to an X-ray tube; the X-ray positioning apparatus is characterized in that the photographing trigger generation apparatus generates the photographing trigger signal, in accordance with a first frame rate and a second frame rate that is higher than the first frame rate, and in that the positioning computer generates the patient platform control data, based on a reference image and one X-ray image selected from consecutively photographed images that are photographed at the second frame rate.

9 Claims, 5 Drawing Sheets

(51) Int. Cl.
*A61B 5/087* (2006.01)
*A61B 5/113* (2006.01)
*A61B 6/04* (2006.01)
*A61B 34/20* (2016.01)
*A61B 90/00* (2016.01)

(52) U.S. Cl.
CPC .......... *A61B 5/1135* (2013.01); *A61B 6/0457* (2013.01); *A61B 6/486* (2013.01); *A61B 6/5235* (2013.01); *A61B 6/54* (2013.01); *A61B 6/541* (2013.01); *A61N 5/10* (2013.01); *A61N 5/1048* (2013.01); *A61N 5/1049* (2013.01); *A61N 5/1069* (2013.01); *A61B 2034/2055* (2016.02); *A61B 2090/376* (2016.02); *A61N 5/1068* (2013.01); *A61N 2005/105* (2013.01); *A61N 2005/1051* (2013.01); *A61N 2005/1056* (2013.01); *A61N 2005/1059* (2013.01); *A61N 2005/1061* (2013.01); *A61N 2005/1062* (2013.01); *A61N 2005/1087* (2013.01); *F04C 2270/041* (2013.01)

(58) Field of Classification Search
CPC .... A61N 2005/1056; A61N 2005/1059; A61N 2005/1061; A61N 2005/1062; A61N 5/1069; A61N 5/107; A61N 5/10
USPC ...................................................... 378/65, 68
See application file for complete search history.

(56) References Cited

U.S. PATENT DOCUMENTS

| | | | | |
|---|---|---|---|---|
| 6,118,848 A * | 9/2000 | Reiffel | ................ | A61N 5/1049 378/162 |
| 6,307,914 B1 * | 10/2001 | Kunieda | ................ | A61B 6/12 378/65 |
| 6,516,046 B1 * | 2/2003 | Fröhlich | ................ | A61B 6/04 378/205 |
| 6,535,574 B1 * | 3/2003 | Collins | ................ | A61N 5/1049 378/20 |
| 6,574,500 B2 * | 6/2003 | Keren | ................ | A61B 6/504 378/51 |
| 7,085,347 B2 * | 8/2006 | Mihara | ................ | A61N 5/10 378/197 |
| 7,171,257 B2 * | 1/2007 | Thomson | ................ | A61N 5/1049 378/69 |
| 7,177,386 B2 * | 2/2007 | Mostafavi | ................ | A61B 5/1135 378/4 |
| 7,204,640 B2 * | 4/2007 | Fu | ................ | A61N 5/1049 378/205 |
| 7,221,733 B1 * | 5/2007 | Takai | ................ | A61N 5/1042 378/65 |
| 7,227,925 B1 * | 6/2007 | Mansfield | ................ | A61N 5/1049 378/41 |
| 7,343,189 B2 * | 3/2008 | Kagermeier | ................ | A61B 6/08 378/20 |
| 7,349,522 B2 * | 3/2008 | Yan | ................ | A61B 5/0816 378/65 |
| 7,453,976 B1 * | 11/2008 | Yin | ................ | A61B 6/032 378/65 |
| 7,453,984 B2 * | 11/2008 | Chen | ................ | A61N 5/1049 378/65 |
| 7,505,809 B2 * | 3/2009 | Strommer | ................ | A61B 5/0555 600/411 |
| 7,570,738 B2 * | 8/2009 | Khamene | ................ | A61B 6/032 378/20 |
| 7,620,144 B2 * | 11/2009 | Bodduluri | ................ | A61B 6/02 378/41 |
| 7,672,429 B2 * | 3/2010 | Urano | ................ | A61N 5/1049 378/65 |
| 7,711,087 B2 * | 5/2010 | Mostafavi | ................ | A61B 6/025 378/22 |
| 7,713,205 B2 * | 5/2010 | Fu | ................ | A61B 8/08 600/437 |
| 7,720,196 B2 * | 5/2010 | Zhang | ................ | A61B 5/113 378/65 |
| 7,853,308 B2 * | 12/2010 | Sauer | ................ | A61N 5/1049 378/62 |
| 7,894,649 B2 * | 2/2011 | Fu | ................ | A61N 5/1049 378/65 |
| 7,924,971 B2 * | 4/2011 | Knox | ................ | A61B 6/5217 378/8 |
| 7,934,869 B2 * | 5/2011 | Ivanov | ................ | A61N 5/1049 378/20 |
| 7,935,939 B2 * | 5/2011 | Aoi | ................ | A61N 5/1049 250/491.1 |
| 7,953,205 B2 * | 5/2011 | Balakin | ................ | A61N 5/1049 250/492.3 |
| 7,994,481 B2 * | 8/2011 | Yagi | ................ | A61B 6/032 250/363.09 |
| 8,042,209 B2 * | 10/2011 | D'Souza | ................ | A61N 5/1049 5/610 |
| 8,086,004 B2 * | 12/2011 | Kuduvalli | ................ | G06T 7/33 382/128 |
| 8,129,699 B2 * | 3/2012 | Balakin | ................ | A61N 5/1049 250/396 R |
| 8,130,907 B2 * | 3/2012 | Maurer, Jr. | ................ | A61B 6/12 378/65 |
| 8,170,319 B2 * | 5/2012 | Shukla | ................ | A61N 5/1049 378/65 |
| 8,274,243 B2 * | 9/2012 | Harada | ................ | A61N 5/1049 250/505.1 |
| 8,295,435 B2 * | 10/2012 | Wang | ................ | A61N 5/10 378/65 |
| 8,315,356 B2 * | 11/2012 | Core | ................ | A61N 5/1049 378/205 |
| 8,345,821 B2 * | 1/2013 | Sumanaweera | ................ | A61N 5/1049 378/65 |
| 8,373,143 B2 * | 2/2013 | Balakin | ................ | A61N 5/1049 250/492.1 |
| 8,379,792 B2 * | 2/2013 | Saito | ................ | A61B 6/032 378/8 |
| 8,399,866 B2 * | 3/2013 | Balakin | ................ | A61N 5/10 250/396 R |
| 8,422,631 B2 * | 4/2013 | Takahashi | ................ | A61N 5/103 378/65 |
| 8,487,278 B2 * | 7/2013 | Balakin | ................ | G21K 1/087 250/492.1 |
| 8,519,365 B2 * | 8/2013 | Balakin | ................ | A61N 5/10 250/492.3 |
| 8,569,717 B2 * | 10/2013 | Balakin | ................ | A61N 5/10 250/396 ML |
| 8,598,543 B2 * | 12/2013 | Balakin | ................ | A61N 5/10 250/396 R |
| 8,614,429 B2 * | 12/2013 | Balakin | ................ | A61N 5/10 250/396 R |
| 8,624,528 B2 * | 1/2014 | Balakin | ................ | A61N 5/10 250/396 R |
| 8,642,978 B2 * | 2/2014 | Balakin | ................ | A61N 5/1049 250/396 R |
| 8,731,268 B2 * | 5/2014 | Li | ................ | A61B 6/032 382/131 |
| 8,747,382 B2 * | 6/2014 | D'Souza | ................ | A61B 5/1135 604/500 |
| 8,784,290 B2 * | 7/2014 | Sumanaweera | ................ | A61B 5/0422 600/1 |
| 8,792,613 B2 * | 7/2014 | Gardner | ................ | A61B 5/04021 378/65 |
| 8,824,630 B2 * | 9/2014 | Maurer, Jr. | ................ | G06F 19/3481 378/20 |
| 8,874,187 B2 * | 10/2014 | Thomson | ................ | A61B 6/032 378/62 |
| 8,901,509 B2 * | 12/2014 | Balakin | ................ | G21K 1/087 250/396 ML |
| 8,917,813 B2 * | 12/2014 | Maurer, Jr. | ................ | A61N 5/10 378/197 |
| 9,108,048 B2 * | 8/2015 | Maurer, Jr. | ................ | A61B 6/5247 |
| 9,248,312 B2 * | 2/2016 | Li | ................ | A61N 5/1049 |

(56) References Cited

U.S. PATENT DOCUMENTS

| | | | |
|---|---|---|---|
| 9,271,692 B2* | 3/2016 | Mostafavi | A61B 5/055 |
| 9,370,330 B2* | 6/2016 | Quam | G21K 1/046 |
| 9,403,034 B2* | 8/2016 | Stancanello | A61B 6/025 |
| 2004/0092813 A1 | 5/2004 | Takizawa et al. | |
| 2007/0211856 A1 | 9/2007 | Urano et al. | |
| 2009/0001276 A1 | 1/2009 | Yagi et al. | |
| 2009/0110238 A1 | 4/2009 | Li et al. | |
| 2010/0067660 A1 | 3/2010 | Maurer, Jr. et al. | |
| 2010/0166145 A1 | 7/2010 | Umekawa et al. | |
| 2012/0121068 A1 | 5/2012 | Maurer, Jr. et al. | |

FOREIGN PATENT DOCUMENTS

| | | |
|---|---|---|
| JP | 3972236 B2 | 9/2007 |
| JP | 2008-206971 A | 9/2008 |
| JP | 2010-063725 A | 3/2010 |
| JP | 2010-154874 A | 7/2010 |
| JP | 2011-500263 A | 1/2011 |
| JP | 2012-501792 A | 1/2012 |

OTHER PUBLICATIONS

Extended European Search Report dated Feb. 18, 2016, issued by the European Patent Office in corresponding European Application No. 12880734.4. (10 pages).

European Search Report dated Mar. 31, 2017, issued by the European Patent Office in corresponding European Application No. 12880734.4. (5 pages).

* cited by examiner

X-RAY POSITIONING APPARATUS, X-RAY POSITIONING METHOD, AND ATTENTIONAL IMAGE PHOTOGRAPHING METHOD

TECHNICAL FIELD

The present invention relates to an X-ray positioning apparatus that performs positioning of a patient at a radiation irradiation position planned in a treatment plan by use of an X-ray image, in a radiation therapy system that irradiates a radiation such as an X-ray, a gamma ray, or a particle beam onto a diseased site of the patient so as to perform medical treatment.

BACKGROUND ART

In recent years, as far as radiation therapy systems for cancer treatment are concerned, cancer treatment systems (particularly, referred to as particle beam therapy systems) utilizing a particle beam such as a proton or a heavy ion have been developed and constructed. As is well known, in comparison with a conventional radiation therapy utilizing an X-ray, a gamma ray, or the like, a particle beam therapy utilizing a particle beam enables intensive irradiation onto a cancer diseased site, i.e., a particle beam can be irradiated in a pin-point manner along the shape of the diseased site; therefore, treatment can be performed without providing any effect to normal cells.

In the case where irradiation onto a diseased site such as a lung or a liver accompanied by respiratory movement is implemented, there has been implemented respiration-synchronized irradiation in which by use of a respiration detection signal from a respiration detector, a charged particle beam is irradiated in synchronization with the respiration. For example, Patent Document 1 discloses a particle beam irradiation apparatus that generates a respiration gate signal for allowing launch of a charged particle beam, based on a body-surface position detected by a respiration detector, and controls a synchrotron and a beam transport apparatus, based on the respiration gate signal. Patent Document 2 discloses a radiation therapy system that is provided with two kinds of monitoring apparatuses, i.e., an external monitoring apparatus (X-ray fluoroscope) for monitoring respiratory signals such as a body deformation amount and a respiratory air amount that can be monitored from the outside of a body and an internal monitoring apparatus for monitoring a respiratory phase based on information about the position of a treatment target, a bone, the diaphragm, or a marker embedded in the body, and that photographs an X-ray fluoroscopic image in synchronization only with the respiratory phase necessary for respiration-synchronized irradiation so as to realize high-accuracy respiration-synchronized irradiation with a few X-ray exposure dose.

In particle beam therapy, it is important that regardless of whether or not respiration-synchronized irradiation is implemented, a particle beam is accurately irradiated onto a diseased site such as a cancer. Accordingly, when undergoing a particle beam therapy, the patient is fixed, by use of a fixing device or the like, on a treatment table (patient platform) in a treatment room (an irradiation room) so that his position does not shift. In order to accurately position a diseased site such as a cancer within a radiation irradiation range, the position of a patient is roughly set by use of a laser pointer or the like and then the diseased site of the patient is precisely positioned by use of an X-ray image or the like.

However, in order to accurately position a diseased site such as a lung or a liver accompanied by respiratory movement, it is required that based on consecutively photographed images outputted from an X-ray image-capturing device and respiratory waveforms outputted from a respiration detector, an X-ray image is obtained at a timing when the position of the respiratory-movement diseased site relatively stabilizes, for example, at a timing of expiration and is utilized for positioning.

PRIOR ART REFERENCE

Patent Document

[Patent Document 1] Japanese Patent Application Laid-Open No. 2010-63725 (Paragraphs 0067 through 0072, FIG. 3)

[Patent Document 2] Japanese Patent Application Laid-Open No. 2010-154874 (Paragraphs 0012 through 0015, FIGS. 1 through 4)

DISCLOSURE OF THE INVENTION

Problems to be Solved by the Invention

In the particle beam irradiation apparatus disclosed in Patent Document 1, a synchrotron and a beam transport apparatus are controlled based on the respiration gate signal generated from the position of a body surface detected by the respiration detector; however, in the case where when a patient is fixed on a treatment platform, accurate positioning is not implemented, high-accuracy radiation therapy cannot be performed. In addition, in the radiation therapy system disclosed in Patent Document 2, an X-ray fluoroscopic image is photographed in synchronization only with the respiratory phase necessary for respiration-synchronized irradiation so that high-accuracy respiration-synchronized irradiation is realized with a few X-ray exposure dose; however, as described above, in the case where when a patient is fixed on a treatment platform, accurate positioning is not implemented, high-accuracy radiation therapy cannot be performed.

When in respiration-synchronized irradiation, patient positioning for fixing a patient on a treatment platform is implemented, a respiration detector may also be utilized. In this case, it is readily conceivable that a function of adding a postscript of respiratory information to an X-ray image is provided; however, the foregoing function is not required in finding the timing when the position of a respiratory-movement diseased site relatively stabilizes. Therefore, the function of adding a postscript of respiratory information to an X-ray image does not make it possible by itself to perform efficient photographing in accordance with the state of a respiratory waveform.

The objective of the present invention is to obtain an X-ray positioning apparatus that can perform efficient photographing in accordance with the state of a respiratory waveform when a patient of radiation therapy is positioned.

Means for Solving the Problems

An X-ray positioning apparatus according to the present invention includes an X-ray video device that obtains first X-ray image data outputted from an X-ray detector for detecting an X-ray radiated by an X-ray tube and generates second X-ray image data in which a respiratory signal related to respiration of a patient and the first X-ray image data are related to each other; a positioning computer that compares a diseased site in the second X-ray image data with a diseased site in a reference image, which is a positioning reference, calculates a postural correction amount in such a way that an actual posture coincides with the posture in a treatment plan, and then generates patient platform control data for controlling a patient platform; and a photographing trigger generation apparatus that outputs a photographing trigger signal for radiating X-rays in accordance with two or more frame rates to the X-ray tube, based on the respiratory signal and a frame rate control signal including photographing conditions for consecutively photographed images in the first X-ray image data. The X-ray positioning apparatus is characterized in that the photographing trigger generation apparatus generates the photographing trigger signal, in accordance with a first frame rate and a second frame rate that is higher than the first frame rate, and in that the positioning computer generates the patient platform control data, based on the reference image and one X-ray image selected from the consecutively photographed images, in the second X-ray image data, that are photographed at the second frame rate.

Advantage of the Invention

The X-ray positioning apparatus according to the present invention generates a photographing trigger signal for radiating X-rays in accordance with two or more frame rates, based on the respiratory signal and a frame rate control signal including photographing conditions for consecutively photographed images; therefore, when a patient in radiation therapy is positioned, photographing can efficiently be implemented in accordance with the state of the respiratory waveform.

MODES FOR CARRYING OUT THE INVENTION

Embodiment 1

Figure 1:
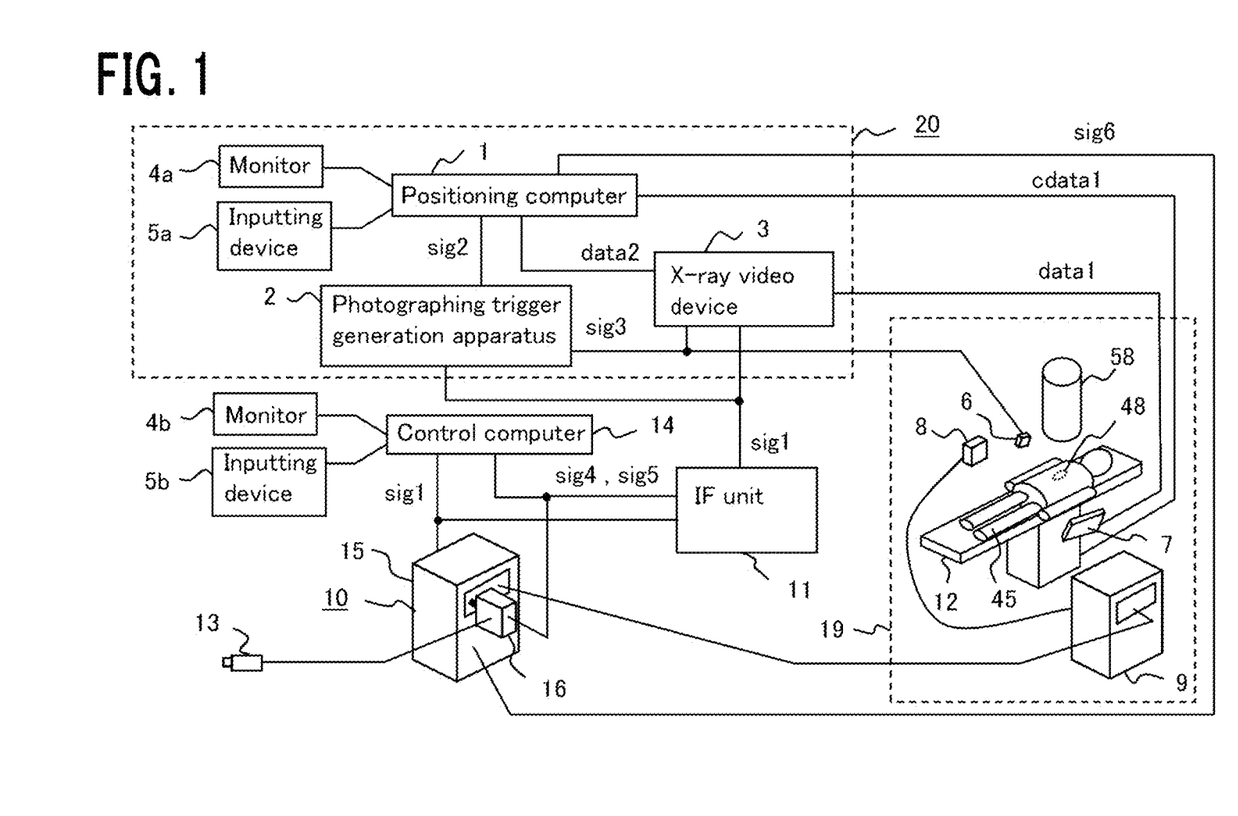
FIG. 1 is a diagram representing the configuration of an X-ray positioning apparatus and schematically illustrating the configuration of a respiration-synchronized irradiation system according to the present invention.
Figure 2:
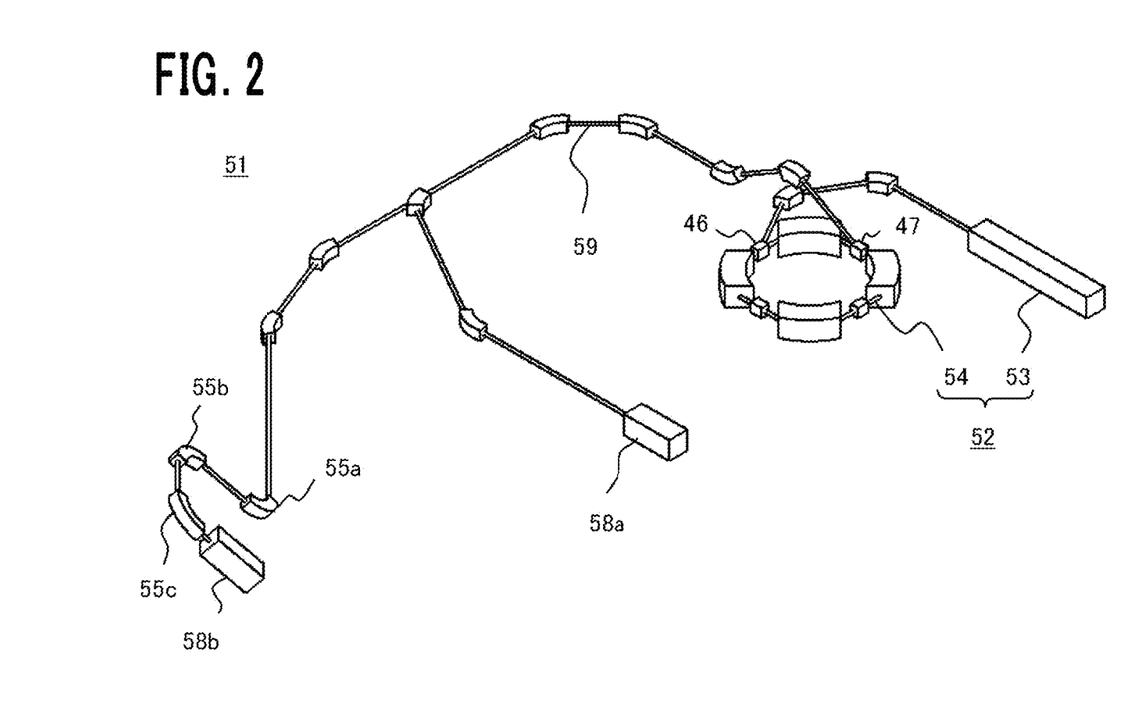
FIG. 2 is a schematic configuration diagram of a particle beam therapy system to which the present invention is applied.
Figure 3:
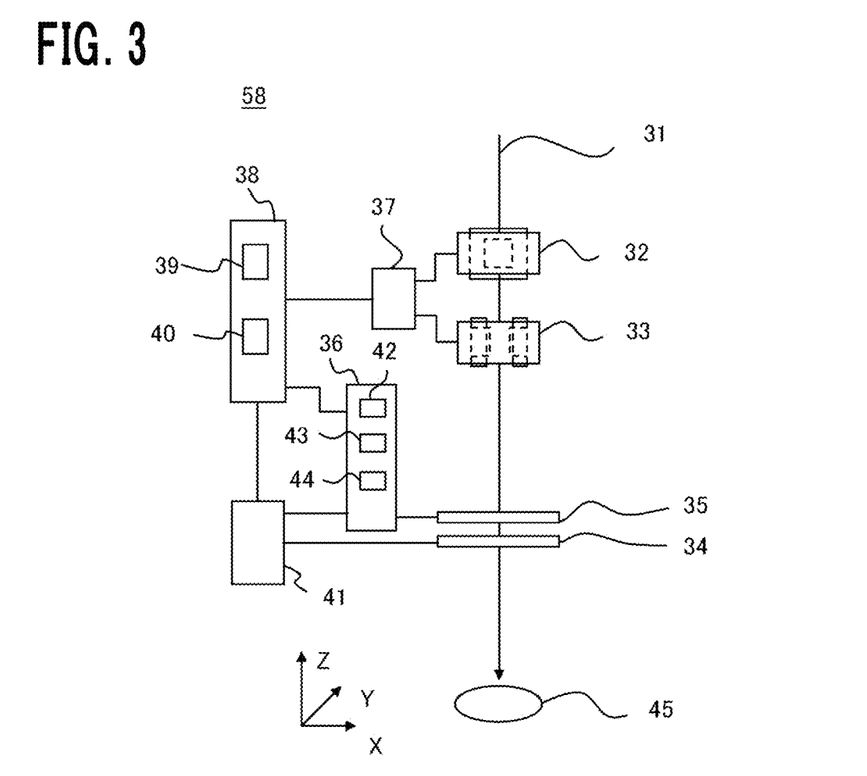
FIG. 3 is a diagram representing the configuration of a particle beam irradiation apparatus in each of FIGS. 1 and 2.
Figure 4:
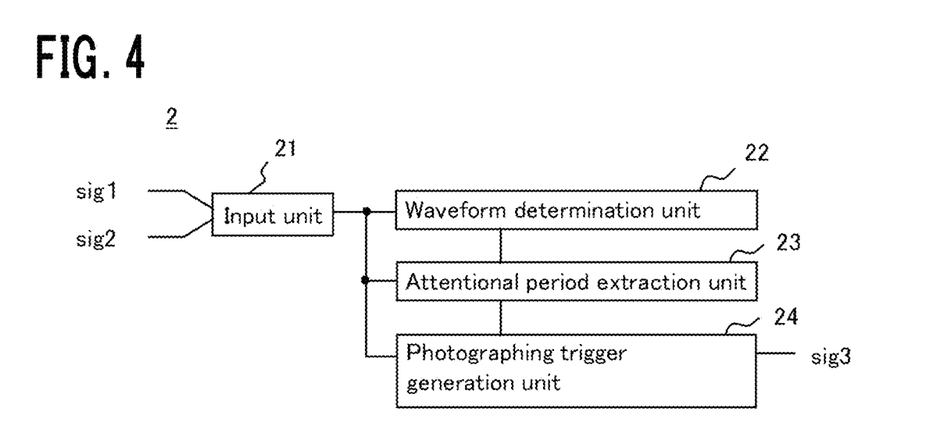
FIG. 4 is a diagram representing the configuration of a photographing trigger generation apparatus in FIG. 1.

FIG. 1 is a diagram representing the configuration of an X-ray positioning apparatus and schematically illustrating the configuration of a respiration-synchronized irradiation system according to the present invention. FIG. 2 is a schematic configuration diagram of a particle beam therapy system to which the present invention is applied; FIG. 3 is a diagram representing the configuration of a particle beam irradiation apparatus in each of FIGS. 1 and 2. FIG. 4 is a diagram representing the configuration of a photographing trigger generation apparatus according to the present invention. The respiration-synchronized irradiation system is provided with an X-ray positioning apparatus 20, a particle beam irradiation apparatus 58, a patient platform 12 on which a patient 45 is placed, a respiration sensor 8, a sense amplifier 9, an X-ray tube 6, an X-ray detector 7, a respiration synchronization signal generator 10, a control computer 14, an IF (interface) unit 11, and a display monitor 4b and an inputting device 5b connected with the control computer 14. The X-ray positioning apparatus 20 is provided with a positioning computer 1, a photographing trigger generation apparatus 2, a display monitor 4a and an inputting device 5a connected with the positioning computer 1, and an X-ray video device 3. The respiration synchronization signal generator 10 is provided with a waveform generator 15, an IF converter 16, and a switch 13. The photographing trigger generation apparatus 2 is provided with an input unit 21, a waveform determination unit 22, an attentional period extraction unit 23, and a photographing trigger generation unit 24.

When a radiation therapy is implemented, the patient 45 is fixed by use of a fixing device or the like (unillustrated) in such a way that the position thereof does not shift with respect to the patient platform 12 in an irradiation room 19. In order to accurately position a diseased site 48 such as a cancer in a radiation irradiation zone, setting such as rough patient positioning utilizing a laser pointer is implemented. Next, precise positioning of the diseased site 48 of the patient 45 is implemented by use of the X-ray positioning apparatus 20.

When precise positioning is implemented, the X-ray positioning apparatus 20 obtains a respiratory signal sig1 from respiratory information on the patient 45 detected by the respiration sensor 8, by way of the sense amplifier 9, the respiration synchronization signal generator 10, and the IF unit 11. The respiratory signal sig1 is a signal related to respiration of the patient 45. The sense amplifier 9 amplifies respiratory information on the patient 45, and the respiration synchronization signal generator 10 generates the respiratory signal sig1, which is a digital signal, from the respiratory information, which is an analogue signal. The IF unit 11 outputs the respiratory signal sig1, and a synchronization signal sig4 and an interlock signal sig5 at a time of respiration-synchronized irradiation to the X-ray positioning apparatus 20, an after-mentioned irradiation management apparatus 38, and the others.

For the respiration sensor 8, the following methods may be utilized. For example, there are conceivable a method of detecting the flow of expired air by means of a flow sensor, a method of measuring the temperature change, due to inspiration, in the vicinity of nasal cavities through image processing by a thermistor or an infra-red camera, a method of detecting the abdominal movement of the patient 45 by means of a position sensitive detector (position sensor) that senses a laser-beam source mounted on the abdomen, and a method of converting the abdominal movement of the patient 45 into a signal by means of a laser displacement gauge.

The X-ray positioning apparatus 20 compares the position of the diseased site 48 of the patient 45 in an X-ray image obtained by making the X-ray detector 7 detect and photograph X-rays radiated from the X-ray tube 6 with the position of the diseased site 48 of the patient 45 in a reference image for positioning obtained from treatment-plan CT image data or the like, calculates a postural correction amount in such a way that the actual posture coincides with the treatment-plan posture, and then outputs patient platform control data cdata1, which is a postural correction amount, to the patient platform 12. Based on the patient platform control data cdata1, which is a postural correction amount, the X-ray positioning apparatus 20 controls the patient platform 12 so as to perform positioning so that the diseased site 48 at a time of therapy is positioned at the beam irradiation center in a radiation therapy. The method of positioning utilizing the respiratory signal sig1 will be described later.

FIG. 2 is a schematic configuration diagram of a particle beam therapy system to which the present invention is applied; FIG. 3 is a diagram representing the configuration of the particle beam irradiation apparatus in each of FIGS. 1 and 2. In FIG. 2, a particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a charged particle accelerator 54. The particle beam irradiation apparatus 58b is provided in a rotating gantry (unillustrated). The particle beam irradiation apparatus 58a is provided in an irradiation room where no rotating gantry is installed. The function of the beam transport system 59 is to achieve communication between the charged particle accelerator 54 and the particle beam irradiation apparatuses 58a and 58b. Part of the beam transport system 59 is provided in the rotating gantry (unillustrated), and that part includes a plurality of deflection electromagnets 55a, 55b, and 55c.

A charged particle beam, which is a particle beam such as a proton beam generated in the ion source, is accelerated by the prestage accelerator 53 and is injected into the charged particle accelerator 54 through an injector 46. The charged particle accelerator 54 is, for example, a synchrotron. The charged particle beam is accelerated to gain predetermined energy. The charged particle beam launched from a launching apparatus 47 of the charged particle accelerator 54 is transported to the particle beam irradiation apparatuses 58a and 58b by way of the beam transport system 59. The particle beam irradiation apparatuses 58a and 58b each irradiate the charged particle beam onto the diseased site 48 of the patient 45. As the reference numerals of the particle beam irradiation apparatuses, "58" is collectively utilized; however, in the case where the particle beam irradiation apparatuses are separately explained, "58a" and "58b" are utilized.

A charged particle beam 31 generated in the beam generation apparatus 52 and accelerated to gain predetermined energy is led to the particle beam irradiation apparatus 58 by way of the beam transport system 59. In FIG. 3, the particle beam irradiation apparatus 58 is provided with X-direction and Y-direction scanning electromagnets 32 and 33 that scan the charged particle beam 31 in X direction and Y direction, respectively, which are directions perpendicular to the charged particle beam 31; a position monitor 34; a dose monitor 35; a dose data converter 36; a beam data processing apparatus 41; a scanning electromagnet power source 37; and an irradiation management apparatus 38 that controls the particle beam irradiation apparatus 58. The irradiation management apparatus 38 is provided with an irradiation control computer 39 and an irradiation control apparatus 40. The dose data converter 36 is provided with a trigger generation unit 42, a spot counter 43, and an inter-spot counter 44. The traveling direction of the charged particle beam 31 is −Z direction.

The X-direction and Y-direction scanning electromagnets 32 and 33 scan the charged particle beam 31 in the X direction and the Y direction, respectively. The position monitor 34 detects beam information for calculating the passing position (gravity center position) through which the charged particle beam 31 that has been scanned by the X-direction scanning electromagnet 32 and the Y-direction scanning electromagnet 33 passes and the size of the charged particle beam 31. The beam data processing device 41 calculates the passing position (gravity center position) and the size of the charged particle beam 31, based on beam information including a plurality of analogue signals (beam information items) detected by the position monitor 34. Moreover, the beam data processing device 41 generates an abnormality detection signal indicating a positional abnormality or a dimensional abnormality of the charged particle beam 31 and outputs the abnormality detection signal to the irradiation management apparatus 38.

The dose monitor 35 detects the dose of the charged particle beam 31. The irradiation management apparatus 38 controls the irradiation position of the charged particle beam 31 on the diseased site 48 of the patient 45, based on treatment plan data created by an unillustrated treatment planning apparatus; when the dose measured by the dose monitor 35 and converted into digital data by the dose data converter 36 reaches a desired dose, the charged particle beam 31 is stopped. The scanning electromagnet power source 37 changes setting currents for the X-direction scanning electromagnet 32 and the Y-direction scanning electromagnet 33, based on control inputs (commands), which are outputted from the irradiation management apparatus 38, to the X-direction scanning electromagnet 32 and the Y-direction scanning electromagnet 33.

In this Description, the scanning irradiation method for the particle beam irradiation apparatus 58 is the raster-scanning irradiation method in which when the irradiation position of the charge particle beam 31 is changed, the charged particle beam 31 is not stopped, i.e., as is the case with the spot scanning irradiation method, the beam irradiation position travels through spot positions one after another. The spot counter 43 measures the irradiation dose for a time during which the beam irradiation position of the charged particle beam 31 is stopped. The inter-spot counter 44 measures the irradiation dose for a time during which the beam irradiation position of the charged particle beam 31 moves. The trigger generation unit 42 generates a dose completion signal when the dose of the charged particle beam 31 at the beam irradiation position reaches the desired irradiation dose.

Figure 5:
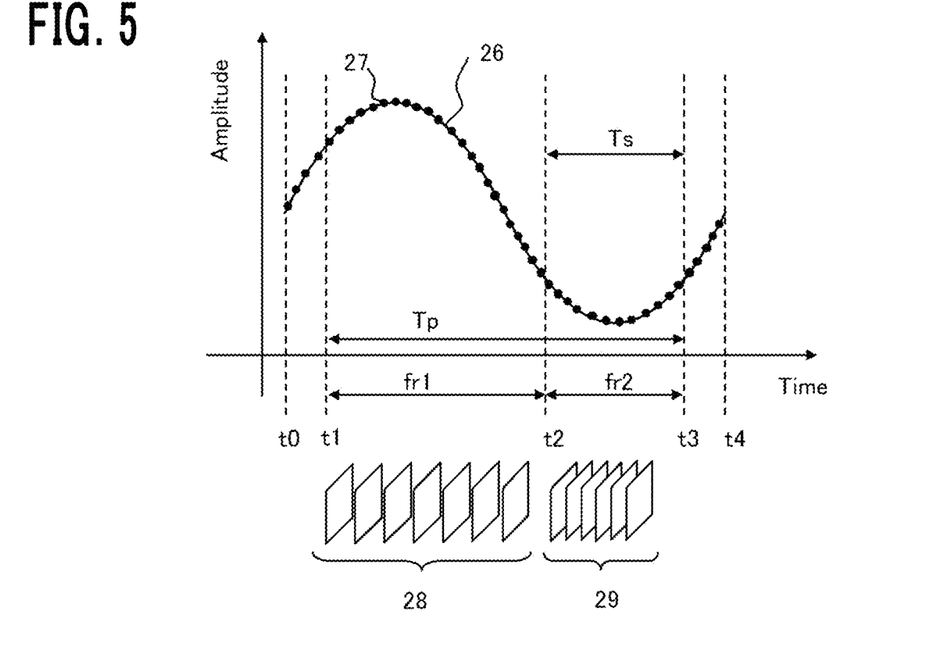
FIG. 5 is a chart for explaining an example of frame-rate changing method according to Embodiment 1 of the present invention.

The method of positioning utilizing the respiratory signal sig1 will be explained. FIG. 5 is a chart for explaining an example of frame-rate changing method according to Embodiment 1 of the present invention. FIG. 5 represents only one cycle of the respiratory waveform 26 of the respiratory signal sig1. The abscissa denotes the time; the ordinate denotes the amplitude. Black circles on the respiratory waveform 26 denote collected data pieces 27 detected with a constant sampling cycle. The respiratory waveform 26 is a curve obtained by supplementing a plurality of collected data pieces 27. The actual respiratory waveform 26 is different from such a sinusoidal wave as represented in FIG. 5; however, explanation will be made under the assumption that the respiratory waveform 26 is a sinusoidal wave. The time period from a time point t0 to a time point t4 is one cycle of the respiratory waveform 26. The portion, of the respiratory waveform 26, where the amplitude thereof is large, suggests that the patient 45 is inhaling; the portion, of the respiratory waveform 26, where the amplitude thereof is small, suggests that the patient 45 is exhaling.

The X-ray video device 3 in the X-ray positioning apparatus 20 obtains X-ray image data data1 in a photographing period Tp. In FIG. 5, the time period from a time point t1 to a time point t3 is the photographing period Tp. The X-ray image data data1 includes consecutively photographed images that have been photographed at two or more frame rates. FIG. 5 represents an example in which switching between two frame rates is made. The X-ray image data data1 includes consecutively photographed images 28 of a frame rate fr1 in the period from the time point t1 to a time point t2 and consecutively photographed images 29 of a frame rate fr2, which is higher than the frame rate fr1, in the period from the time point t2 to the time point t3. In Embodiment 1, there is described an example in which positioning is implemented by use of the X-ray image data data1 in a flat period, of the respiratory waveform 26, where the patient 45 is exhaling. The period from the time point t2 to the time point t3 is an attentional period Ts in which the frame rate is changed.

The X-ray positioning apparatus 20 starts photographing of X-ray images of the diseased site 48 in accordance with photographing conditions, such as the photographing period Tp, the frame rates fr1 and fr2, the frame rate changing time point t2, the attentional period Ts, and the like, that are specified by the inputting devices 5a such as a keyboard, a mouse and the like. The positioning computer 1 outputs to the photographing trigger generation apparatus 2 a frame rate control signal sig2 including the photographing conditions such as the photographing period Tp, the frame rates fr1 and fr2, the frame rate changing time point t2, the attentional period Ts, and the like. The photographing trigger generation apparatus 2 performs a photographing trigger generation procedure. The photographing trigger generation apparatus 2 outputs a photographing trigger signal sig3 to the X-ray tube 6, based on the respiratory signal sig1 inputted from the IF unit 11 and the frame rate control signal sig2. The photographing starting time point t1, the frame rate changing time point t2, and the photographing ending time point t3 are based on one cycle of the respiratory waveform 26.

The X-ray tube 6 radiates an X-ray each time the photographing trigger generation apparatus 2 inputs the photographing trigger signal sig3 thereto. The X-ray detector 7 detects an X-ray that has passed through the patient 45 and then outputs the X-ray image data data1 to the X-ray video device 3. The X-ray video device 3 implements a positioning image data generation procedure. The X-ray video device 3 obtains the X-ray image data data1 from the X-ray detector 7 and then stores in a built-in memory or the like X-ray image data data2 in which the time point of the respiratory waveform 26 and the X-ray image photographing time point are related to each other, based on the respiratory signal sig1 inputted from the IF unit 11 and the photographing trigger signal sig3 inputted from the photographing trigger generation apparatus 2. When the photographing of the X-ray image in the photographing period Tp is completed, the X-ray video device 3 outputs the X-ray image data data2 to the positioning computer 1.

The positioning computer 1 implements a patient platform control data generation procedure. The positioning computer 1 obtains X-ray image data data2. The positioning computer 1 selects one X-ray image, from the X-ray image data data2, that has the state (position, size, and the like) of the diseased site 48 of the patient 45, which is closest to the state (position, size, and the like) of the diseased site 48 of the patient 45 in the positioning reference image obtained from treatment-plan CT image data or the like. The positioning computer 1 compares the position of the diseased site 48 of the patient 45 in the selected X-ray image with the position of the diseased site 48 of the patient 45 in the reference image, calculates a postural correction amount in such a way that the actual posture coincides with the treatment-plan posture, and then outputs patient platform control data cdata1, which is a postural correction amount, to the patient platform 12. The patient platform control data cdata1 includes, for example, 6 flexibility degrees, i.e., 3 parallel translation axes[$\Delta X$, $\Delta Y$, $\Delta Z$] and 3 rotation axes[$\Delta A$, $\Delta B$, $\Delta C$]. In the patient platform 12, motors for 3 parallel translation axes and motors for 3 rotation axes are driven in accordance with the patient platform control data cdata1. As described above, the X-ray positioning apparatus 20 can calculate a postural correction amount in such a way that the actual posture coincides with the treatment-plan posture and can perform positioning in such a way that the diseased site 48 at a time of treatment coincides with the beam irradiation center (isocenter) of radiation therapy.

After the positioning has been completed, the charged particle beam 31 is synchronized with the respiratory state of the patient, so that respiration-synchronized irradiation onto the diseased site 48 of the patient 45 is implemented. During the respiration-synchronized irradiation, the X-ray tube 6 and the X-ray detector 7 are moved from the photographing position so that they do not obstruct irradiation of a radiation. The respiration synchronization signal generator 10 generates the synchronization signal sig4, based on the respiratory information on the patient 45, which is detected by the respiration sensor 8 and then is amplified by the sense amplifier 9, and irradiation feasible period information sig6, which is obtained from the positioning computer 1 and can be regarded as the state of the diseased site 48 at a time when the positioning has been completed.

The interlock signal sig5 is generated by the IF converter 16, by turning on or off of the switch 13. For example, when the switch 13 is turned on, irradiation is allowed, i.e., the interlock is released; when the switch 13 is turned off, irradiation is not allowed, i.e., the interlock operates. When respiration-synchronized irradiation is implemented, the respiratory signal sig1 is transmitted to the control computer 14, and then the control computer 14 displays the respiratory waveform 26, and displays waveforms or the like of the synchronization signal sig4 and the interlock signal sig5 on the display monitor 4b. The switch 13 and the display monitor 4b and the inputting device 5b connected with the control computer 14 are installed in an irradiation control room outside the controlled area.

When the patient is positioned, the X-ray positioning apparatus 20 according to Embodiment 1 extracts a part waveform of the respiratory waveform 26 for a desired period (photographing period Tp), so that there can be obtained consecutively photographed X-ray images (moving images) whose consecutive-photographing frame rate is variable. The period suitable for patient positioning is an approximately resting period in which the diseased site 48 of the patient 45 is at a standstill or approximately at a standstill. The approximately resting period is a period in which respiration-synchronized irradiation can be implemented; a treatment plan is created for the diseased site 48 of the patient 45 in the approximately resting period.

In the photographing trigger generation apparatus 2, the input unit 21 receives the respiratory signal sig1 and the frame rate control signal sig2. The photographing trigger generation apparatus 2, for example, applies a bilinear transformation to the collected data pieces 27 that form the respiratory waveform 26, and determine whether or not the respiratory waveform 26 in the respiratory signal sig1 is in a predetermined state. Specifically, in the case where the difference between the amplitudes of adjacent data pieces is within a predetermined small range, the photographing trigger generation apparatus 2 determines that the respiratory waveform 26 is flat. The determination on whether or not the respiratory waveform 26 is flat is implemented by the waveform determination unit 22. In Embodiment 1, an approximately resting period where the patient 45 is exhaling is extracted; thus, the period where the amplitude of the respiratory waveform 26 is close to the lower limit value and it is determined that the respiratory waveform 26 is flat is extracted as the attentional period Ts. The attentional period Ts is extracted based on the result of the determination by the waveform determination unit 22, the respiratory signal sig1, and the frame rate control signal sig2.

In the case where the respiratory signal sig1 is a waveform signal that is within the photographing period Tp and out of the attentional period Ts, the photographing trigger generation unit 24 outputs the photographing trigger signal sig3 corresponding to the low frame rate fr1, based on the result of the extraction by the attentional period extraction unit 23. In the case where the respiratory signal sig1 is a waveform signal that is within the photographing period Tp and within the attentional period Ts, the photographing trigger generation unit 24 outputs the photographing trigger signal sig3 corresponding to the frame rate fr2 that is higher than the frame rate fr1.

As described above, in the X-ray positioning apparatus 20 according to Embodiment 1, when a patient is positioned, there can be obtained consecutively photographed X-ray images (moving images) whose consecutive-photographing frame rate is variable; therefore, in the attentional period Ts which the operator especially desires to extract, photographing is implemented in a minute manner, and in the other period within the photographing period Tp, photographing is implemented at a frame rate that is as high as the standard frame rate, so that in comparison with a conventional method in which photographing is implemented at a constant frame rate, the image processing amount and the memory amount in the X-ray video device 3 and the positioning computer 1 can be reduced. Accordingly, in comparison with a conventional method in which photographing is implemented at a constant frame rate, the X-ray positioning apparatus 20 according to Embodiment 1 can efficiently photograph X-ray images.

The X-ray positioning apparatus 20 according to Embodiment 1 raises the frame rate so as to photograph minute X-ray images in a period where the respiratory waveform 26 is flat, i.e., in the attentional period Ts in FIG. 5, so that verification of the coincidence with the positioning reference image can be implemented with a great number of X-ray images in detail; therefore, the accuracy of the positioning is raised.

The X-ray positioning apparatus 20 according to Embodiment 1 efficiently photographs X-ray images in a necessary period out of one cycle of the respiratory waveform 26, for example, in the photographing period Tp that is shorter than one cycle, so that unnecessary X-ray dose to the patient 45 can be suppressed. Unlike a conventional method in which when the amplitude of the respiratory waveform 26 exceeds a threshold value, photographing is started, the X-ray positioning apparatus 20 according to Embodiment 1 securely photographs X-ray images at the low frame rate fr2 in a period other than the attentional period Ts; thus, no long-term non-photographing state, which may happen in the conventional method, occurs. Moreover, the X-ray positioning apparatus 20 according to Embodiment 1 does not require the work such as position adjustment for the respiration sensor and adjustment of a threshold value that are implemented in order to prevent the long-term non-photographing state; therefore, working time for positioning can be shortened and hence the efficiency of the work can be raised.

The X-ray positioning apparatus 20 according to Embodiment 1 includes the X-ray video device 3 that obtains the first X-ray image data data1 outputted from the X-ray detector 7 for detecting an X-ray radiated by the X-ray tube 6 and generates the second X-ray image data data2 in which the respiratory signal sig1 related to the respiration of the patient 45 and the first X-ray image data data1 are related to each other; the positioning computer 1 that compares the diseased site 48 in the second X-ray image data data2 with the diseased site 48 in the reference image, which is the positioning reference, calculates a postural correction amount in such a way that the actual posture coincides with the treatment-plan posture, and then generates the patient platform control data cdata1 for controlling the patient platform 12; and the photographing trigger generation apparatus 2 that outputs to the X-ray tube 6 the photographing trigger signal sig3 for radiating X-rays in accordance with two or more frame rates fr1 and fr2, based on the frame rate control signal sig2 including the photographing conditions for consecutively photographed images 28 and 29 in the X-ray image data data1 and the respiratory signal sig1. The X-ray positioning apparatus 20 according to Embodiment 1 is characterized in that the photographing trigger generation apparatus 2 generates the photographing trigger signal sig3 in accordance with the first frame rate fr1 and the second frame rate fr2 that is higher than the first frame rate fr1, and in that the positioning computer 1 generates the patient platform control data cdata1, based on the reference image and one X-ray image selected from consecutively photographed images 29, in the second X-ray image data data2, that are photographed at the second frame rate fr2. Because having the foregoing characteristics, the X-ray positioning apparatus 20 according to Embodiment 1 can generate the photographing trigger signal sig3 for radiating X-rays in accordance with two or more frame rates fr1 and fr2, based on the frame rate control signal sig2 including the photographing conditions for consecutively photographed images 28 and 29 and the respiratory signal sig1; therefore, when a patient in radiation therapy is positioned, photographing can efficiently be implemented in accordance with the state of the respiratory waveform 26.

An X-ray positioning method according to Embodiment 1 includes a positioning image data generation procedure in which there is obtained the first X-ray image data data1 outputted from the X-ray detector 7 for detecting an X-ray radiated by the X-ray tube 6 and there is generated the second X-ray image data data2 in which the respiratory signal sig1 related to the respiration of the patient 45 and the first X-ray image data data1 are related to each other; a patient platform control data generation procedure in which the diseased site 48 in the second X-ray image data data2 is compared with the diseased site 48 in the reference image, which is the positioning reference, a postural correction amount is calculated in such a way that the actual posture coincides with the treatment-plan posture, and then the patient platform control data cdata1 for controlling the patient platform 12 is generated; and a photographing trigger generation procedure in which the photographing trigger signal sig3 for radiating X-rays in accordance with two or more frame rates fr1 and fr2 is outputted to the X-ray tube 6, based on the frame rate control signal sig2 including the photographing conditions for consecutively photographed images 28 and 29 in the X-ray image data data1 and the respiratory signal sig1. The X-ray positioning method according to Embodiment 1 is characterized in that in the photographing trigger generation procedure, the photographing trigger signal sig3 is generated in accordance with the first frame rate fr1 and the second frame rate fr2 that is higher than the first frame rate fr1, and in that in the patient platform control data generation procedure, the patient platform control data cdata1 is generated, based on the reference image and one X-ray image selected from consecutively photographed images 29, in the second X-ray image data data2, that are photographed at the second frame rate fr2. Because having the foregoing characteristics, the X-ray positioning method according to Embodiment 1 can generate the photographing trigger signal sig3 for radiating X-rays in accordance with two or more frame rates fr1 and fr2, based on the frame rate control signal sig2 including the photographing conditions for consecutively photographed images 28 and 29 and the respiratory signal sig1; therefore, when a patient in radiation therapy is positioned, photographing can efficiently be implemented in accordance with the state of the respiratory waveform 26.

Embodiment 2

Figure 6:
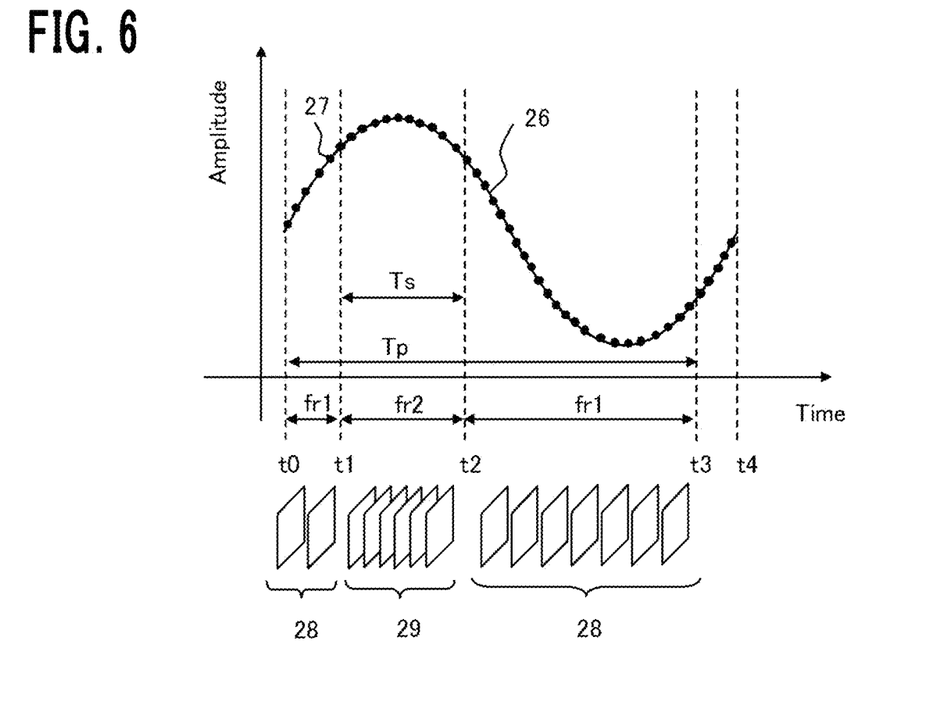
FIG. 6 is a chart for explaining an example of frame-rate changing method according to Embodiment 2 of the present invention.

FIG. 6 is a chart for explaining an example of frame-rate changing method according to Embodiment 2 of the present invention. In Embodiment 2, there is described an example in which positioning is implemented by use of the X-ray image data data1 in a flat period, of the respiratory waveform 26, where the patient 45 is inhaling. That is to say, in the X-ray positioning apparatus 20 according to Embodiment 2, the period corresponding to the flat portion of the respiratory waveform 26 at a time when the patient 45 is inhaling is referred to as the attentional period Ts. FIG. 6 represents only one cycle (from a time point t0 to a time point t4) of the respiratory waveform 26 of the respiratory signal sig1. FIG. 6 represents an example in which switching between two frame rates is made. In FIG. 6, the time period from the time point t0 to a time point t3 is the photographing period Tp. The X-ray image data data1 includes consecutively photographed images 28 of the frame rate fr1 in the periods from the time point t0 to a time point t1 and from a time point t2 to the time point t3 and consecutively photographed images 29 of the frame rate fr2, which is higher than the frame rate fr1, in the period from the time point t1 to the time point t2. The time period from the time point t1 to the time point t2 is the attentional period Ts. In Embodiment 2, the positioning reference image is an image at a time when the patient 45 is inhaling.

The X-ray positioning apparatus 20 according to Embodiment 2 can demonstrate the same effect as the X-ray positioning apparatus 20 according to Embodiment 1; therefore, when a patient in radiation therapy is positioned, photographing can efficiently be implemented in accordance with the state of the respiratory waveform 26. Depending on the diseased site 48 of the patient 45, the approximately resting period at a time when the patient 45 is inhaling may longer than the approximately resting period at a time when the patient 45 is exhaling. In the case where the approximately resting period at a time when the patient 45 is inhaling is longer than the approximately resting period at a time when the patient 45 is exhaling, the X-ray positioning apparatus 20 according to Embodiment 2 can raise the accuracy of positioning, in comparison with Embodiment 1 in which the attentional period Ts is set in the period where the patient 45 is exhaling. In addition, because the approximately resting period is long, the therapy time in which the respiration-synchronized irradiation is implemented can be shortened.

Embodiment 3

Figure 7:
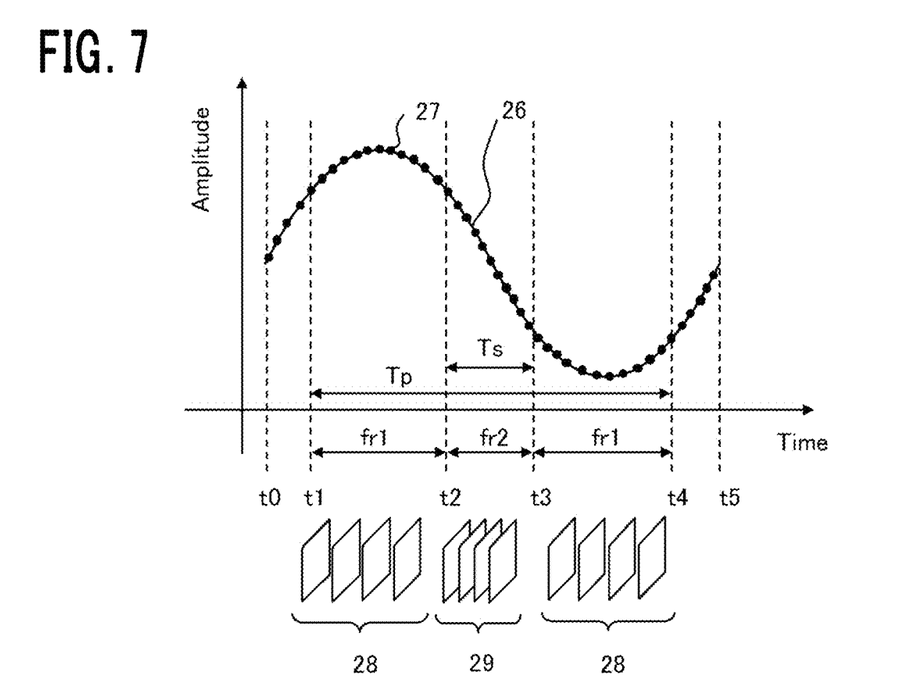
FIG. 7 is a chart for explaining an example of frame-rate changing method according to Embodiment 3 of the present invention.

FIG. 7 is a chart for explaining an example of frame-rate changing method according to Embodiment 3 of the present invention. In Embodiment 3, there will be explained an example in which the attentional period Ts is set in a period where the respiratory waveform 26 changes steeply. In Embodiment 3, when a treatment plan for the diseased site 48 of the patient 45 is created or other case, the diseased site 48 is consecutively photographed, in order to obtain consecutively photographed images, as the attentional images. FIG. 7 represents only one cycle (from a time point t0 to a time point t5) of the respiratory waveform 26 of the respiratory signal sig1. FIG. 7 represents an example in which switching between two frame rates is made. In FIG. 7, the time period from a time point t1 to a time point t4 is the photographing period Tp. The X-ray image data data1 includes consecutively photographed images 28 of the frame rate fr1 in the periods from the time point t1 to a time point t2 and from a time point t3 to the time point t4 and consecutively photographed images 29 of the frame rate fr2, which is higher than the frame rate fr1, in the period from the time point t2 to the time point t3. The time period from the time point t2 to the time point t3 is the attentional period Ts.

In general, the moving speed of the diseased site 48 such as a lung or a liver accompanied by respiratory movement increases in a period where the respiratory waveform 26 changes steeply. When the attentional period Ts is set in a period where the respiratory waveform 26 changes steeply, an image having a small blur caused by movement can be obtained; thus, it is made possible to understand the details of the movement of an organ. In comparison with the case where photographing is implemented at a constant frame rate, it is made possible to understand the details of the movement of an organ with a small X-ray dose. By understanding the details of the movement of an organ, the direction of irradiation onto the diseased site 48 avoiding sound organs and the irradiation period for implementing respiration-synchronized irradiation can appropriately be set in creating of a treatment plan. Even when a treatment plan for the diseased site 48 of the patient 45 is not created, the diseased site 48 may consecutively be photographed, in order to obtain consecutively photographed images, as the attentional images.

The attentional image photographing method according to Embodiment 3 is characterized by including a photographing trigger signal generation procedure for determining a steep period where the waveform of the respiratory signal sig1 steeply changes and generating the photographing trigger signal sig3 in accordance with a third frame rate (the frame rate fr2) that is higher than the first frame rate fr1; an attentional period extraction procedure for determining whether or not a given period is a steep period where the waveform of the respiratory signal sig1 steeply changes and extracting the steep period as the attentional period Ts; and an attentional image data generation procedure for making the X-ray video device 3 obtain the first X-ray image data data1 and generate the second X-ray image data data2 in which the respiratory signal sig1 and the first X-ray image data data1 are related to each other. The attentional image photographing method according to Embodiment 3 has the foregoing characteristics; therefore, the direction of irradiation onto the diseased site 48 avoiding sound organs and the irradiation period for implementing respiration-synchronized irradiation can appropriately be set in creating of a treatment plan.

In the scope of the present invention, the embodiments thereof can be combined with one another and can appropriately be modified or omitted.

DESCRIPTION OF REFERENCE NUMERALS

1: positioning computer
2: photographing trigger generation apparatus
3: X-ray video device
6: X-ray tube
7: X-ray detector
12: patient platform
20: X-ray positioning apparatus
22: waveform determination unit
23: attentional period extraction unit
24: photographing trigger generation unit
28, 29: consecutively photographed images
45: patient
48: diseased site
sig1: respiratory signal
sig2: frame rate control signal
sig3: photographing trigger signal
fr1, fr2: frame rate
data1, data2: X-ray image data
cdata1: patient platform control data
Tp: photographing period
Ts: attentional period

The invention claimed is:

1. An X-ray positioning apparatus that controls a patient platform by use of an X-ray image so as to position a diseased site of a patient at a radiation irradiation position planned in a treatment plan, the X-ray positioning apparatus comprising:
   an X-ray video device including (i) a receiving device for receiving first X-ray image data, from an X-ray detector that detects an X-ray radiated by an X-ray tube, and (ii) a built-in memory for storing the received first X-ray image data, said X-ray video device being configured to generate second X-ray image data in which a respiratory signal related to respiration of the patient and the first X-ray image data are related to each other;
   a positioning computer that compares a diseased site in the second X-ray image data with a diseased site in a reference image, which is a positioning reference, calculates a postural correction amount in such a way that an actual posture coincides with a posture in the treatment plan, and then generates patient platform control data for controlling the patient platform; and
   a signal generator that communicates with the X-ray tube and generates a trigger signal for radiating X-rays in accordance with two or more frame rates based on (i) the respiratory signal and (ii) a frame rate control signal including photographing conditions for consecutively photographed images in the first X-ray image data,
   wherein the signal generator generates the trigger signal, in accordance with a first frame rate and a second frame rate that is higher than the first frame rate, and
   wherein the positioning computer generates the patient platform control data, based on the reference image and one X-ray image selected from consecutively photographed images, in the second X-ray image data, that are photographed at the second frame rate.

2. The X-ray positioning apparatus according to claim 1, wherein the signal generator is further configured to
   (i) determine whether or not a waveform of the respiratory signal is in a predetermined state,
   (ii) extract an attentional period where, based on a result of said determination, the consecutively photographed images are taken at the second frame rate, and
   (iii) output the trigger signal, based on a photographing period and the attentional period in the frame rate control signal.

3. The X-ray positioning apparatus according to claim 2, wherein the signal generator further determines whether or not a given period is a flat period where a waveform of the respiratory signal is within a predetermined small range, and extracts, as the attentional period, a period that is determined as the flat period and in which an amplitude of the respiratory signal is near a lower limit value.

4. The X-ray positioning apparatus according to claim 2, wherein the signal generator further determines whether or not a given period is a flat period where the waveform of the respiratory signal is within a predetermined small range, and extracts, as the attentional period, a period that is determined as the flat period and in which an amplitude of the respiratory signal is near an upper limit value.

5. An X-ray positioning method in which a patient platform is controlled by use of an X-ray image so as to position a diseased site of a patient at a radiation irradiation position planned in a treatment plan, the X-ray positioning method comprising:
   a positioning image data generation procedure, executed by an X-ray video device, in which there is obtained, by a receiving device of the X-ray video device, first X-ray image data outputted from an X-ray detector for detecting an X-ray radiated by an X-ray tube and stored in a built-in memory of said X-ray video device, and there is generated second X-ray image data in which a respiratory signal related to respiration of the patient and the first X-ray image data are related to each other;
   a patient platform control data generation procedure, executed by a positioning computer, in which a diseased site in the second X-ray image data is compared with a diseased site in a reference image, which is a positioning reference, a postural correction amount is calculated in such a way that an actual posture coincides with the posture in the treatment plan, and then patient platform control data for controlling the patient platform is generated; and
   a trigger generation procedure, in which a trigger signal for radiating X-rays in accordance with two or more frame rates is generated based on the respiratory signal and a frame rate control signal including photographing conditions for consecutively photographed images in the first X-ray image data,
   wherein in the trigger generation procedure, the trigger signal is generated in accordance with a first frame rate and a second frame rate that is higher than the first frame rate, and
   wherein in the patient platform control data generation procedure, the patient platform control data is generated, based on the reference image and one X-ray image selected from the consecutively photographed images, in the second X-ray image data, that are photographed at the second frame rate.

6. An attentional image photographing method in which the consecutively photographed images of the diseased site are taken by use of the X-ray positioning apparatus according to claim 1, the attentional image photographing method comprising:
- a trigger signal generation procedure for determining a steep period where a waveform of the respiratory signal steeply changes and generating the trigger signal in accordance with a third frame rate that is higher than the first frame rate;
- an attentional period extraction procedure for determining whether or not a given period is a steep period where a waveform of the respiratory signal steeply changes and extracting the steep period as an attentional period where the consecutively photographed images are taken at the third frame rate; and
- an attentional image data generation procedure for making the X-ray video device obtain first X-ray image data and generate second X-ray image data in which the respiratory signal and the first X-ray image data are related to each other.

7. An attentional image photographing method in which the consecutively photographed images of the diseased site are taken by use of the X-ray positioning apparatus according to claim 2, the attentional image photographing method comprising:
- a trigger signal generation procedure for determining a steep period where a waveform of the respiratory signal steeply changes and generating the trigger signal in accordance with a third frame rate that is higher than the first frame rate;
- an attentional period extraction procedure for determining whether or not a given period is a steep period where a waveform of the respiratory signal steeply changes and extracting the steep period as an attentional period where the consecutively photographed images are taken at the third frame rate; and
- an attentional image data generation procedure for making the X-ray video device obtain first X-ray image data and generate second X-ray image data in which the respiratory signal and the first X-ray image data are related to each other.

8. An attentional image photographing method in which the consecutively photographed images of the diseased site are taken by use of the X-ray positioning apparatus according to claim 3, the attentional image photographing method comprising:
- a trigger signal generation procedure for determining a steep period where a waveform of the respiratory signal steeply changes and generating the trigger signal in accordance with a third frame rate that is higher than the first frame rate;
- an attentional period extraction procedure for determining whether or not a given period is a steep period where a waveform of the respiratory signal steeply changes and extracting the steep period as an attentional period where the consecutively photographed images are taken at the third frame rate; and
- an attentional image data generation procedure for making the X-ray video device obtain first X-ray image data and generate second X-ray image data in which the respiratory signal and the first X-ray image data are related to each other.

9. An attentional image photographing method in which the consecutively photographed images of the diseased site are taken by use of the X-ray positioning apparatus according to claim 4, the attentional image photographing method comprising:
- a trigger signal generation procedure for determining a steep period where a waveform of the respiratory signal steeply changes and generating the trigger signal in accordance with a third frame rate that is higher than the first frame rate;
- an attentional period extraction procedure for determining whether or not a given period is a steep period where a waveform of the respiratory signal steeply changes and extracting the steep period as an attentional period where the consecutively photographed images are taken at the third frame rate; and
- an attentional image data generation procedure for making the X-ray video device obtain first X-ray image data and generate second X-ray image data in which the respiratory signal and the first X-ray image data are related to each other.

* * * * *